US012779283B2

(12) United States Patent
Jung et al.

(10) Patent No.: US 12,779,283 B2
(45) Date of Patent: Nov. 3, 2026

(54) WORKOUT IMAGE DISPLAY METHOD AND ELECTRONIC DEVICE

(71) Applicant: Samsung Electronics Co., Ltd., Suwon-si (KR)

(72) Inventors: Bosung Jung, Suwon-si (KR); Seunggu Kang, Suwon-si (KR); Jihae Ko, Suwon-si (KR); Sangmi Kim, Suwon-si (KR); Taehwan Son, Suwon-si (KR); Moonbae Song, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 555 days.

(21) Appl. No.: 18/352,661

(22) Filed: Jul. 14, 2023

(65) Prior Publication Data

US 2023/0356028 A1 Nov. 9, 2023

Related U.S. Application Data

(63) Continuation of application No. PCT/KR2022/000772, filed on Jan. 14, 2022.

(30) Foreign Application Priority Data

Feb. 8, 2021 (KR) ........................ 10-2021-0017860

(51) Int. Cl.
*A63B 24/00* (2006.01)
*A61B 5/00* (2006.01)
(Continued)

(52) U.S. Cl.
CPC ........ *A63B 24/0006* (2013.01); *A61B 5/0022* (2013.01); *A61B 5/681* (2013.01);
(Continued)

(58) Field of Classification Search
None
See application file for complete search history.

(56) References Cited

U.S. PATENT DOCUMENTS

| | | | |
|---|---|---|---|
| 8,502,693 | B2 | 8/2013 | Shum et al. |
| 8,712,510 | B2 | 4/2014 | Quy |

(Continued)

FOREIGN PATENT DOCUMENTS

| | | | | |
|---|---|---|---|---|
| CN | 102945344 A | 2/2013 | | |
| KR | 20130028504 A | * | 3/2013 | ............. G09G 5/005 |

(Continued)

OTHER PUBLICATIONS

International Search Report for PCT/KR2022/000772 mailed Apr. 26, 2022, 4 pages.

(Continued)

*Primary Examiner* — Xuan M Thai
*Assistant Examiner* — Andrew Bodendorf
(74) *Attorney, Agent, or Firm* — Nixon & Vanderhye P.C.

(57) ABSTRACT

According to various embodiments, an electronic device may comprise: a communication module comprising communication circuitry configured to communicate with at least one external electronic device; a memory for storing at least one app; and a processor operatively connected to the communication module and the memory. The processor may be configured to: activate a workout management app (e.g., home gym app) stored in the memory; in response to the execution of the at least one app, identify whether a workout-related content has been executed on the basis of the activated workout management app; display an object for execution of a training program through the workout management app based on the workout-related content being executed; in response to a user input on the object, make an automatic connection with the at least one external elec- (Continued)

tronic device through the communication module; configure, on the basis of at least one piece of workout-related information acquired from the at least one external electronic device, a training program screen into which the workout-related content and the workout-related information are integrated; and display the training program screen through the at least one external electronic device.

20 Claims, 12 Drawing Sheets

(51) Int. Cl.
*A61B 5/024* (2006.01)
*A61B 5/11* (2006.01)

(52) U.S. Cl.
CPC ...... *A63B 24/0062* (2013.01); *A61B 5/02438* (2013.01); *A61B 5/1114* (2013.01); *A61B 5/1128* (2013.01); *A61B 5/6801* (2013.01); *A63B 2024/0009* (2013.01)

(56) References Cited

U.S. PATENT DOCUMENTS 9,785,827 B1 10/2017 Ray
9,954,994 B2* 4/2018 Koo ...................... G06F 1/1632
11,273,343 B2* 3/2022 Augustin ........... A63B 21/4037
11,321,894 B2* 5/2022 Garofalo ................. G06F 3/017
2012/0183939 A1 7/2012 Aragones et al.
2012/0271143 A1 10/2012 Aragones et al.
2013/0316316 A1* 11/2013 Flavell ................... G16H 20/30 434/247
2013/0332631 A1* 12/2013 Lee ......................... G06F 13/10 710/33
2014/0135960 A1 5/2014 Choi
2015/0037771 A1* 2/2015 Kaleal, III ........... G09B 19/003 434/257
2015/0196804 A1* 7/2015 Koduri ............... G06Q 10/0639 482/8
2015/0358201 A1* 12/2015 Park ...................... H04W 12/33 715/735
2016/0086500 A1* 3/2016 Kaleal, III ............... A61B 5/20 434/257
2016/0367857 A1* 12/2016 Aragones ............... A61B 5/681
2016/0381202 A1* 12/2016 Koo ....................... G06F 1/1632 455/559
2017/0061754 A1* 3/2017 Kim .................... H04M 19/047
2017/0239524 A1* 8/2017 Lee ......................... G16H 50/30
2017/0311025 A1* 10/2017 Kim ...................... G06F 3/1454
2017/0348563 A1* 12/2017 Kim ......................... G09B 5/02
2018/0036591 A1* 2/2018 King ........................ H04N 5/76
2018/0063215 A1* 3/2018 Hahm ................... H04L 65/764
2018/0074676 A1* 3/2018 Lee ..................... G06F 3/04842
2018/0140900 A1* 5/2018 Kim ...................... A61B 5/1118
2018/0192893 A1* 7/2018 Magi ...................... A61B 5/681
2018/0196584 A1* 7/2018 Han .................. G06F 16/90344
2018/0205675 A1* 7/2018 Koo ........................ H04W 4/12
2018/0218637 A1 8/2018 Lee et al.
2019/0009136 A1 1/2019 Lee et al.
2019/0105551 A1 4/2019 Ray
2019/0262664 A1* 8/2019 Schindler ........... A63B 24/0075
2019/0313965 A1 10/2019 Dugan
2020/0215390 A1* 7/2020 Shin ..................... A61B 5/6802
2020/0254299 A1 8/2020 Kanuparthi et al.
2021/0005224 A1* 1/2021 Rothschild ........... H04N 9/8205
2021/0065869 A1* 3/2021 Hamill ................... G16H 40/67
2021/0303253 A1* 9/2021 Hwang .................. G06Q 20/02
2022/0047920 A1* 2/2022 Poulin .................... G16H 50/30
2023/0356028 A1* 11/2023 Jung .................... A61B 5/0022

FOREIGN PATENT DOCUMENTS

KR 20140062892 A 5/2014
KR 20150078746 A 7/2015
KR 20150082364 A 7/2015
KR 20150107268 A * 9/2015 ............. G16H 20/30
KR 101582347 B1 1/2016
KR 20160016263 A 2/2016
KR 20170001393 A 1/2017
KR 20180058139 A 5/2018
KR 20180089699 A 8/2018
KR 20190040735 A 4/2019
KR 20200032364 A 3/2020

OTHER PUBLICATIONS

Office Action dated Feb. 2, 2026, with English translation, in Korean Application No. 10-2021-0017860, 21 pp.

* cited by examiner

WORKOUT IMAGE DISPLAY METHOD AND ELECTRONIC DEVICE

CROSS-REFERENCE TO RELATED APPLICATIONS

This application is a continuation of International Application No. PCT/KR2022/000772 designating the United States, filed on Jan. 14, 2022, in the Korean Intellectual Property Receiving Office and claiming priority to Korean Patent Application No. 10-2021-0017860, filed on Feb. 8, 2021, in the Korean Intellectual Property Office, the disclosures of each of which are incorporated by reference herein in their entireties.

BACKGROUND

Field

The disclosure relates to a method for displaying a workout image and an electronic device.

Description of Related Art

With the development of information communication technology and semiconductor technology, various electronic devices are developing into multimedia devices that provide various multimedia services. For example, a portable electronic device may provide various multimedia services such as a broadcasting service, a wireless Internet service, a camera service, and a music playback service.

The electronic device may provide the user with the user's health information (e.g., heart rate information, calorie information, time information) to satisfy the user's interest in health care. The electronic device may be operationally connected to other electronic devices (e.g., wearable devices) located in the vicinity, and may share data (e.g., the user's health information) with each other.

With the development of electronic communication, electronic devices can easily provide users with various workout contents (e.g., home training video contents). For example, the home training video contents may include a guide audio and subtitles so that the user can follow the trainer's movements while watching the video. The electronic device may display video contents related to workout through the display module, but it may be difficult to provide the user with his or her workout process and the amount of change in his biometric information according to the workout.

SUMMARY

Embodiments of the disclosure may provide an electronic device that may be operationally connected to other nearby electronic devices while providing workout-related video content to the user. The electronic device according to an embodiment may acquire information related to the user from the other electronic device and provide the workout-related video contents and the acquired information to the user.

According to various example embodiments, an electronic device may comprise: a communication module comprising communication circuitry configured to communicate with at least one external electronic device; a memory for storing at least one app; and a processor operatively connected to the communication module and the memory. The processor may be configured to: activate a workout management app (e.g., home gym app) stored in the memory; in response to the execution of the at least one app, identify whether a workout-related content has been executed; display an object for execution of a training program through the workout management app based on the workout-related content being executed; in response to an input on the object, make an automatic connection with the at least one external electronic device through the communication module; configure, on the basis of at least one piece of workout-related information acquired from the at least one external electronic device, a training program screen into which the workout-related content and the workout-related information are integrated; and control the external electronic device to display the training program screen.

A method according to various example embodiments may comprise: activating a workout management app for managing a workout; identifying whether workout-related content has been executed based on the activated workout management app in response to the execution of at least one app stored in a memory; based on the workout-related content being executed, displaying an object for executing a training program through the workout management app; in response to an input on the object, making an automatic connection with at least one external electronic device; configuring a training program screen into which the workout-related content and workout-related information are integrated on the basis of at least one workout-related information acquired from the at least one external electronic device; and displaying the training program screen through the at least one external electronic device.

Various example embodiments of the present disclosure, in an electronic device, may detect the playback of workout-related content, display an object for interworking with another electronic device, and, in response to an input to the object, display workout-related content, user's workout and/or the user's biometric information together.

According to an example embodiment, the electronic device may integrate workout-related content, biometric data such as the user's heart rate information and/or calorie consumption, and/or a photographed image of the user and provide it to the user on one screen. Users who perform a home training may maximize and/or improve the effect of their workouts by monitoring their workout progress. In addition, various effects that can be directly or indirectly identified through this disclosure may be provided.

BRIEF DESCRIPTION OF THE DRAWINGS

In connection with the description of the drawings, the same or similar reference numerals may be used for the same or similar elements. Further, the above and other aspects, features and advantages of certain embodiments of the present disclosure will be more apparent from the following detailed description, taken in conjunction with the accompanying drawings, in which.

DETAILED DESCRIPTION

Figure 1:
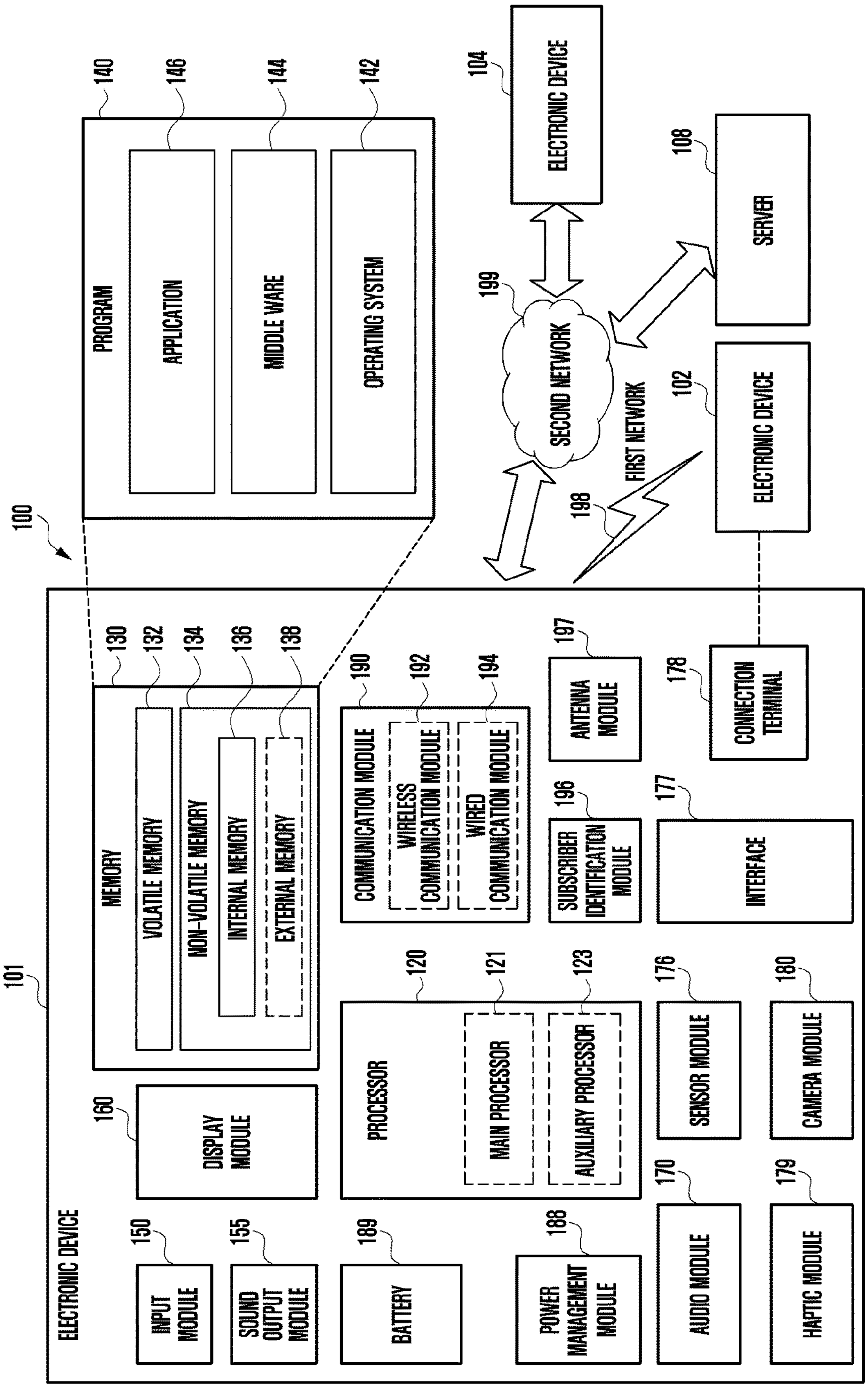
FIG. 1 is a block diagram illustrating an example electronic device in a network environment according to various embodiments.

FIG. 1 illustrates an electronic device in a network environment according to various embodiments. Referring to FIG. 1, an electronic device 101 in a network environment 100 may communicate with an electronic device 102 via a first network 198 (e.g., a short-range wireless communication network), or at least one of electronic device 104 or a server 108 via a second network 199 (e.g., a long-range wireless communication network). The electronic device 101 may communicate with the electronic device 104 via the server 108. The electronic device 101 includes a processor 120, memory 130, an input module 150, an audio output module 155, a display module 160, an audio module 170, a sensor module 176, an interface 177, a connecting terminal 178, a haptic module 179, a camera module 180, a power management module 188, a battery 189, a communication module 190, a subscriber identity module (SIM) 196, or an antenna module 197. In various embodiments, at least one of the components (e.g., the connecting terminal 178) may be omitted from the electronic device 101, or one or more other components may be added in the electronic device 101. In various embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. As at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. The processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). The auxiliary processor 123 (e.g., an ISP or a CP) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134. The non-volatile memory 134 may include an internal memory 136 or external memory 138.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The audio output module 155 may output sound signals to the outside of the electronic device 101. The audio output module 155 may include, for example, a speaker or a receiver. The speaker may be used for general purposes, such as playing multimedia or playing record. The receiver may be used for receiving incoming calls. The receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. The display module 160 may include a touch sensor adapted to detect a touch, or a pressure sensor adapted to measure the intensity of force incurred by the touch.

The audio module 170 may convert a sound into an electrical signal and vice versa. The audio module 170 may obtain the sound via the input module 150, or output the sound via the audio output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. The interface 177 may include, for example, a high definition multimedia interface (HDMI), a universal serial bus (USB) interface, a secure digital (SD) card interface, or an audio interface.

A connection terminal 178 may include a connector via which the electronic device 101 may be physically connected with the external electronic device (e.g., the electronic device 102). The connection terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. The haptic module 179 may include, for example, a motor, a piezoelectric element, or an electric stimulator.

The camera module 180 may capture a still image or moving images. The camera module 180 may include one or more lenses, image sensors, image signal processors, or flashes.

The power management module 188 may manage power supplied to the electronic device 101. The power management module 188 may be implemented as at least part of, for example, a power management integrated circuit (PMIC).

The battery 189 may supply power to at least one component of the electronic device 101. The battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the AP) and supports a direct (e.g., wired) communication or a wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or a standard of the Infrared Data Association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. The antenna module 197 may include an antenna including a radiating element including a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190

(e.g., the wireless communication module 192) from the plurality of antennas. The signal or the power may then be transmitted or received between the communication module 190 and the external electronic device via the selected at least one antenna. Another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

Commands or data may be transmitted or received between the electronic device 101 and the external electronic device 104 via the server 108 coupled with the second network 199. Each of the electronic devices 102 or 104 may be a device of a same type as, or a different type, from the electronic device 101. All or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
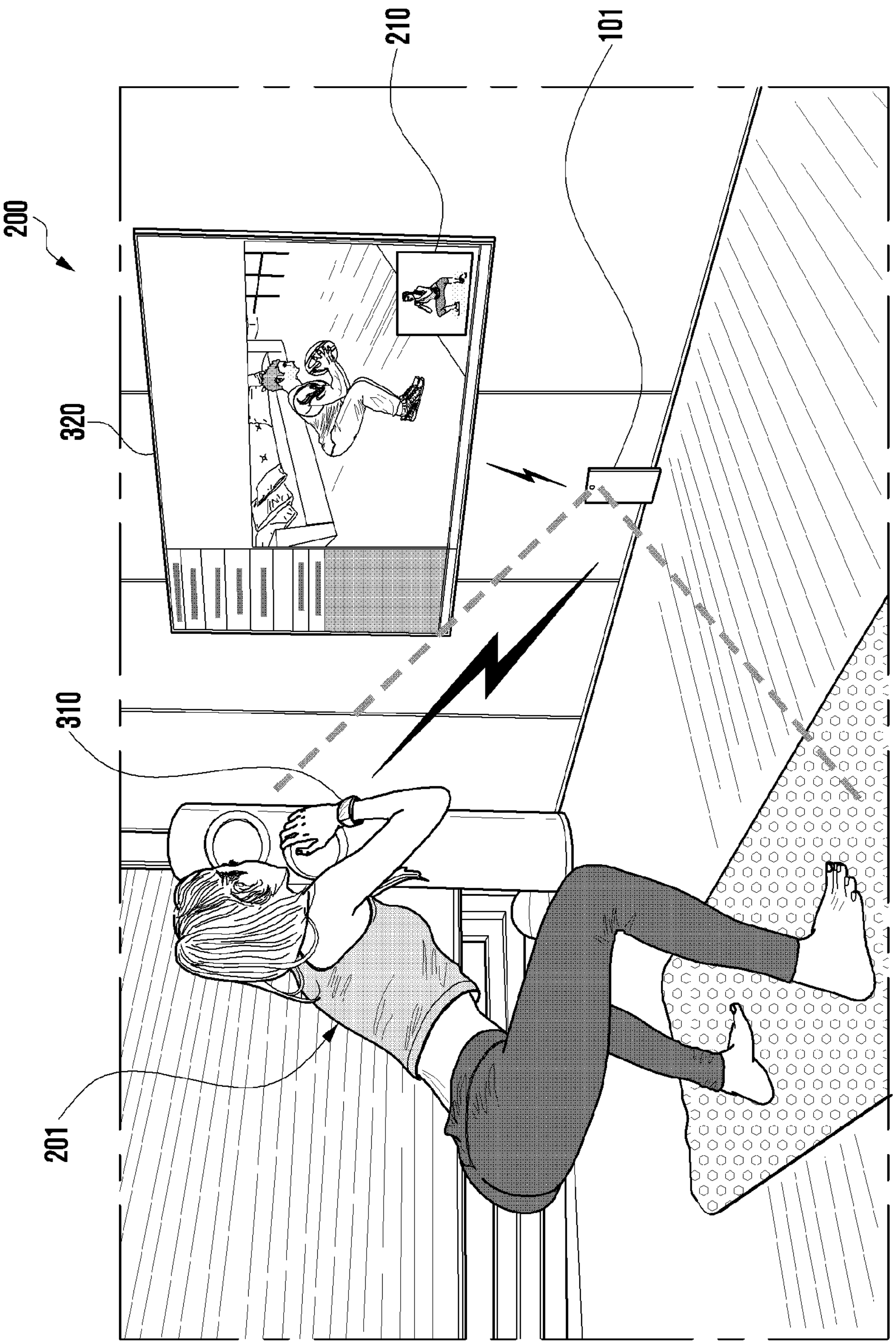
FIG. 2 is a diagram illustrating a user performing a home training while watching workout-related content according to various embodiments.

FIG. 2 is a diagram illustrating an example in which a user performs a home training while watching workout-related content according to various embodiments.

With the growing interest in health, the demand for home training is increasing. Home training may refer, for example, to a method in which the user performs a workout alone indoors. For example, home training may include a workout method in which workout-related content is played on a display device, and the user follows the workout while watching the played-up workout-related content.

With reference to FIG. 2, an embodiment 200 in which the user 201 performs home training while watching workout-related content is shown. According to an embodiment, the electronic device 101 may be operatively connected to at least one external electronic device (e.g., the wearable device 310 and/or the display device 320) and may at least partially control the at least one external electronic device. The electronic device 101 may share data with at least one external electronic device. For example, the wearable device 310 may be worn on the wrist of the user 201 and acquire biometric information (e.g., a heart rate, a body temperature, a movement, and/or a posture of the user 201) of the user 201 and transmit the acquired biometric information to the electronic device 101. When playing back workout-related content, the electronic device 101 may transmit the workout-related content to the operatively connected display device 320 and control the display device 320 so that the workout-related content is played back in the display device 320. According to an embodiment, the electronic device 101 may photograph the workout of the user 201 using a disposed camera module (e.g., the camera module 180 of FIG. 1), and the photographed image data 210 may be transmitted to the display device 320. For example, the display device 320 may display the received image data 210 (e.g., an image in which the workout scene of the user 201 is photographed). According to an embodiment, the electronic device 101 may transmit and receive data to/from at least one external electronic device in real time or at predetermined time intervals.

With reference to FIG. 2, the electronic device 101 may transmit workout-related content to the display device 320 and control the display device 320 so that the workout-related content is played (e.g., displayed) through the display device 320. The user 201 may perform the workout in the same manner as the workout scene included in the workout-related content played back through the display device 320. The wearable device 310 mounted on the wrist of the user 201 may continuously measure and/or acquire health information of the user 201. The electronic device 101 may acquire health information of the user 201 from the wearable device 310 mounted on the wrist of the user 201 during workout and may display health information through the display device 320. The electronic device 101 may photograph the workout scene of the user 201 using the camera module 180 and play back the photographed image 210. The electronic device 101 may at least partially control the display device 320 to display the photographed image 210 through the display device 320. According to an embodiment, the electronic device 101 may display a workout-related content, a health information of the user 201, and/or a photographed image 210 of the workout scene of the user 201 together through the display device 320. According to an embodiment, the user 201 may improve convenience and maximize and/or improve the workout effect in performing home training.

According to an embodiment, the electronic device 101 may install a workout management app (e.g., a home training program, a home gym application) for providing an image related to home training to a user in a memory (e.g., the memory 130 of FIG. 1). The electronic device 101 may execute a home gym app to provide workout-related content to a user based on the home gym app. According to an embodiment, a home gym may be defined as a workout method in which a user follows a workout posture while watching a workout-related video (e.g., workout-related content) at home. For example, a home gym may be a workout method that involves at least one of yoga, pilates, stretching, aerobics, and/or core workouts. According to an embodiment, the electronic device 101 may execute a home gym app and provide a home gym service (e.g., providing a user with workout-related content (e.g., workout image) related to the home gym) to the user based on the home gym app. According to an embodiment, the electronic device 101 may be operationally connected to at least one external electronic device (e.g., the wearable device 310 and the display device 320), and the wearable device 310 may be used to acquire the user's health information (e.g., biometric information). The electronic device 101 may provide workout-related content and the user's health information to the user through the display device 320 using the home gym app. The electronic device 101 may provide a home gym service to the user based on the home gym app. Hereinafter, the home gym refers to a workout method in which the user follows the workout posture while watching a workout-related video at home, and the home gym app may refer, for example, to a program that efficiently provides a home gym service to the user.

Figure 3:
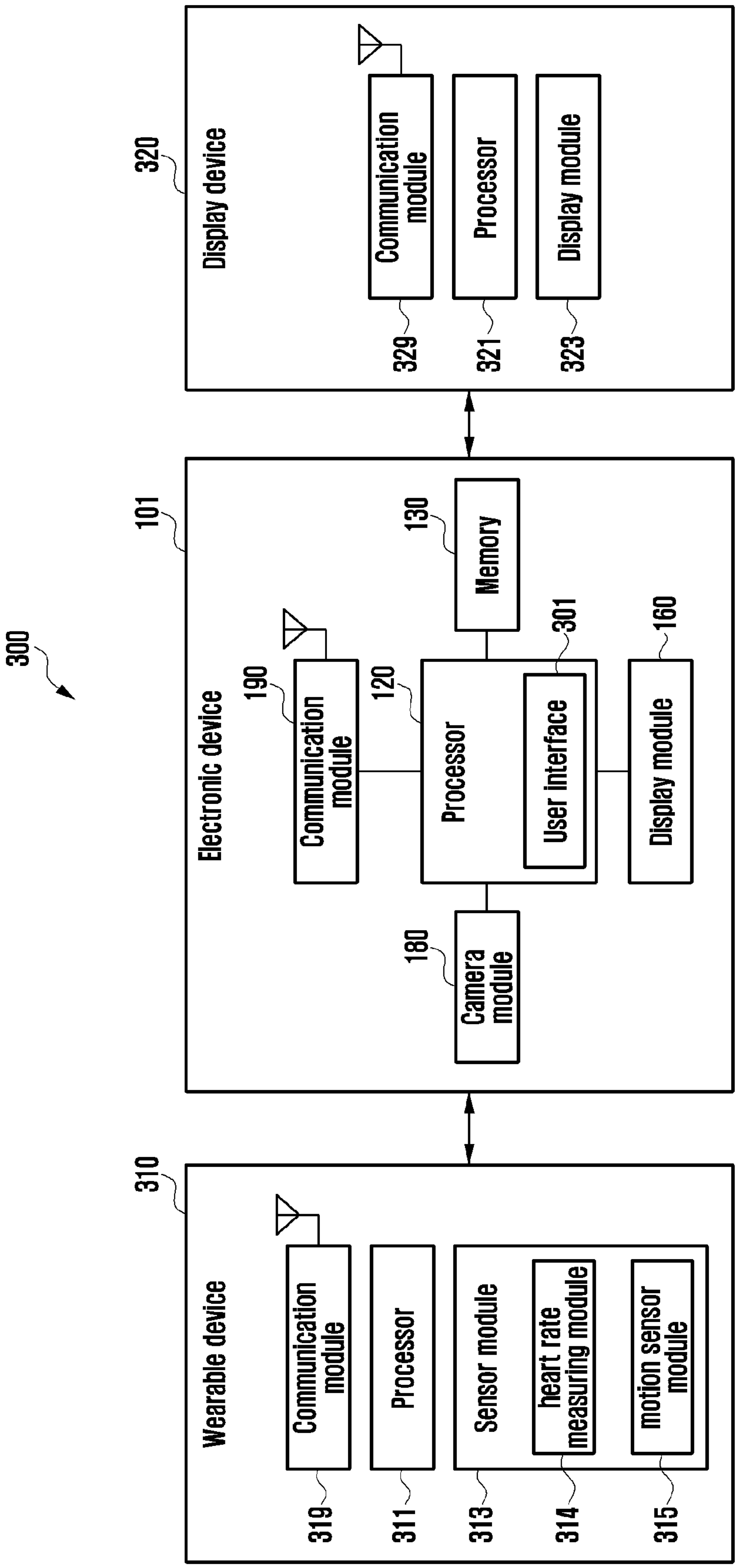
FIG. 3 is a block diagram illustrating an example configuration of an electronic device and an external electronic device according to various embodiments.

FIG. 3 is a block diagram 300 illustrating an example configuration of an electronic device and an external electronic device according to various embodiments.

According to various embodiments, the electronic device (e.g., the electronic device 101 of FIG. 1) may be operatively connected to at least one external electronic device (e.g., the wearable device 310 and/or the display device 320) and may share data with each other. The electronic device 101 may at least partially control the at least one external electronic device. For example, the electronic device 101 may acquire the health information of the user measured using the wearable device 310. The electronic device 101 may play back workout-related content through the display device 320. According to an embodiment, the electronic device 101 may reconfigure the user interface (UI) so that the user's health information is included in the workout-related content in playing back workout-related content through the display device 320 and may play back the reconstructed user interface.

With reference to FIG. 3, the electronic device 101 may include a processor (e.g., including processing circuitry) (e.g., the processor 120 of FIG. 1), a memory (e.g., the memory 130 of FIG. 1), a display module (e.g., including a display) (e.g., the display module 160 of FIG. 1), a camera module (e.g., including a camera) (e.g., the camera module 180 of FIG. 1), and/or a communication module (e.g., including communication circuitry) (e.g., the communication module 190 of FIG. 1).

The processor 120 may include various processing circuitry and execute a program (e.g., the program 140 of FIG. 1) stored in the memory 130 to control at least one other component (e.g., hardware or software component) and perform various data processing or operations. According to an embodiment, as at least part of the data processing or operation, the processor 120 may store instructions or data received from other components (e.g., the display module 160, the camera module 180, or the communication module 190) in the memory 130. According to an embodiment, the processor 120 may generate a user interface 301 based on the configuration information and may display the user interface 301 through the display module 160. For example, when the processor 120 executes a home gym application, the processor 120 may generate a user interface 301 corresponding to the home gym application and may display the user interface 301 through the display module 160.

The memory 130 may store various data used by at least one component of the electronic device 101 (e.g., the processor 120, the display module 160, the camera module 180, and/or the communication module 190). The data may include, for example, input data or output data for software (e.g., the program 140 of FIG. 1) and related commands. According to an embodiment, the processor 120 may acquire data from at least one external electronic device (e.g., the wearable device 310 and/or the display device 320) and store the acquired data in the memory 130.

The display module 160 may include a display and visually provide the user with at least one content. For example, the processor 120 may generate a user interface 301 and display the generated user interface 301 through the display module 160. For example, when a home gym application is executed, the processor 120 may generate a user interface 301 corresponding to the home gym application and display it through the display module 160.

The camera module 180 may include a camera and record still images or moving images and may include at least one of at least one lens, an image sensor, an image signal processor, and/or a flash. According to an embodiment, the processor 120 may photograph a user's workout scene using the camera module 180 and display the photographed image through the display module 160. The processor 120 may provide a real-time recorded image to the user.

The communication module 190 may include various communication circuitry and establish a direct (e.g., wired) communication channel or wireless communication channel between the electronic device 101 and at least one external electronic device (e.g., the wearable device 310 and/or the display device 320) and may assist in performing communication through the established communication channel. According to an embodiment, the electronic device 101 may perform wireless communication with at least one external electronic device using the communication module 190 and share data with each other. The electronic device 101 may at least partially control the at least one external electronic device.

With reference to FIG. 3, the wearable device 310 may include a processor (e.g., including processing circuitry) 311, a sensor module (e.g., including at least one sensor) 313, and/or a communication module (e.g., including communication circuitry) 319. According to an embodiment, the wearable device 310 may be mounted in at least partial contact with the user's body and may measure and acquire health information such as biometric information of the user. For example, the wearable device 310 may include a wearable watch mounted on the user's wrist. The wearable device 310 may perform wireless communication with the electronic device 101 through the communication module 319 and may be at least partially controlled by the electronic device 101.

The processor 311 of the wearable device 310 may include various processing circuitry and measure the heart rate of the user using the heart rate measurement module (e.g., including various processing circuitry and/or executable program instructions) 314 included in the sensor module 313. For example, the wearable device 310 may be mounted on the user's wrist, and the heart rate measurement module 314 may be disposed in response to a vascular position located on the user's wrist. The heart rate measurement module 314 may measure the user's heart rate based on blood flow through the user's blood vessels. The heart rate measurement module 314 may measure the user's heart rate in real time or at predetermined time intervals.

The processor 311 of the wearable device 310 may detect the user's movement using the motion sensing module (e.g., including various processing circuitry and/or executable program instructions) 315 included in the sensor module 313. For example, the motion sensing module 315 may include at least one sensor of a gyro sensor, an acceleration sensor, and/or a motion sensor and may detect the user's movement.

The processor 311 of the wearable device 310 may perform wireless communication with the electronic device 101 through the communication module 319 and may transmit the data measured or acquired using the sensor module 313 to the electronic device 101. According to an embodiment, the electronic device 101 may at least partially control the wearable device 310. For example, the electronic device 101 may control the wearable device 310 so that the wearable device 310 provides the electronic device 101 with the health information of the user measured by the wearable device 310 using the sensor module 313.

With reference to FIG. 3, the display device 320 may include a processor 321, a display module (e.g., including a display) 323, and/or a communication module (e.g., including communication circuitry) 329. According to an embodiment, the display device 320 may visually provide at least one content to the user through the display module 323. The display device 320 may display a still image or video through the display module 323. For example, the display device 320 may include a television or a monitor. The display device 320 may perform wireless communication with the electronic device 101 through the communication module 329 and may be at least partially controlled by the electronic device 101.

The processor 321 of the display device 320 may include various processing circuitry and provide visual information to the user using the display module 323. The display device 310 may perform wireless communication with the electronic device 101 through the communication module 319 and may visually display at least one content received from the electronic device 101 through the display module 323. For example, the display device 320 may receive a user interface from the electronic device 101 and display the user interface through the display module 323 under the control of the electronic device 101.

Figure 4:
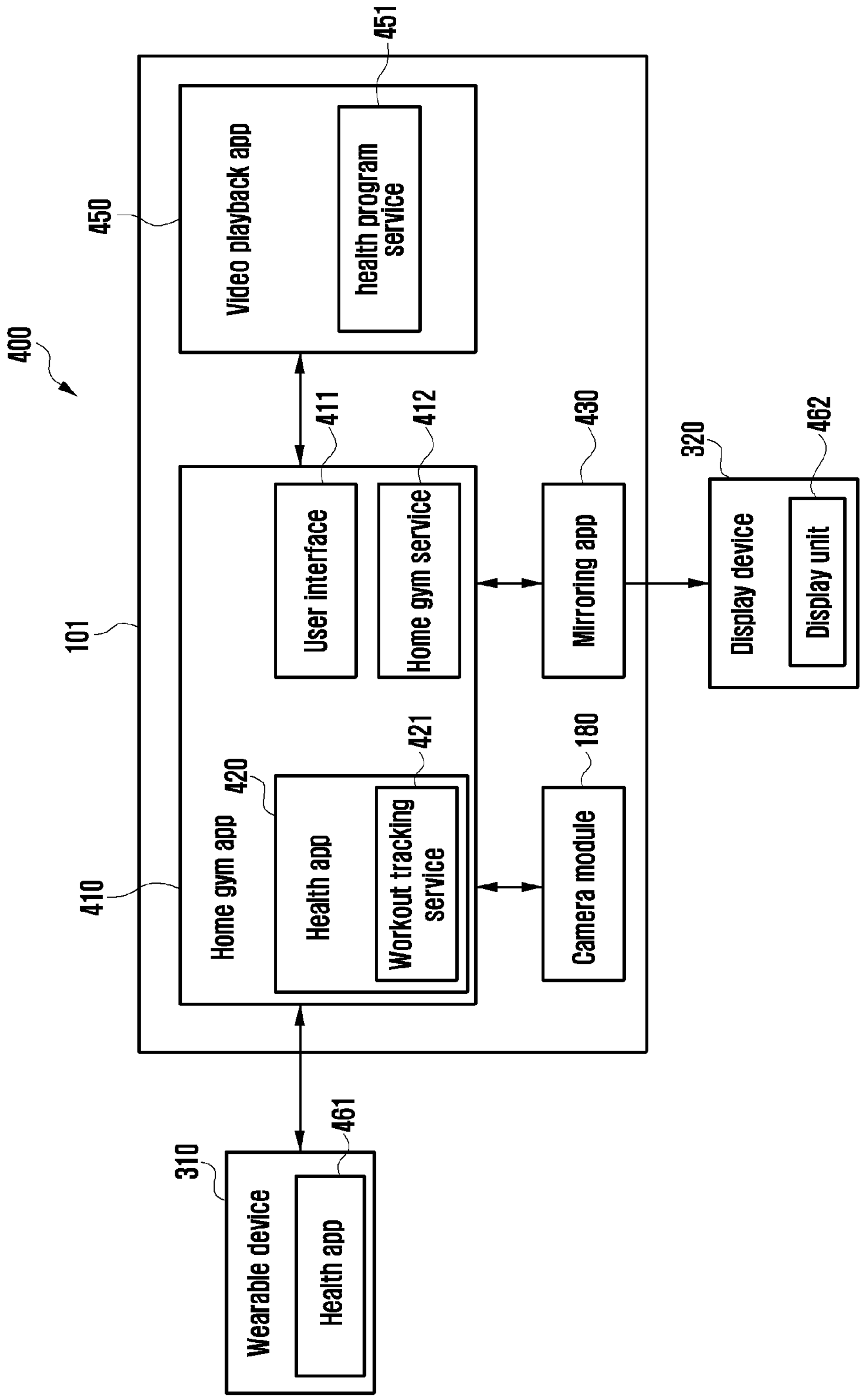
FIG. 4 is a diagram illustrating an example operation of displaying a workout image in an electronic device interlocked with an external electronic device according to various embodiments.

FIG. 4 is a diagram 400 illustrating an example operation of displaying a workout image in an electronic device interlocked with an external electronic device according to various embodiments.

According to various embodiments, the electronic device (e.g., the electronic device 101 of FIG. 1) may be operatively connected to at least one external electronic device (e.g., the wearable device 310 and/or the display device 320) and may at least partially control the at least one external electronic device. According to an embodiment, the electronic device 101 may provide a home gym service to a user who wants home training (e.g., a home gym). Home training (e.g., home gym) may be a method of performing a workout alone while the user watches a workout related video indoors, and the electronic device 101 may provide a home gym service to improve the user's workout effect through home training. For example, home training may be a workout method of performing at least one of yoga, pilates, stretching, aerobics, and/or core workouts as a workout method in which generally the user follows the workout movements and workout postures of the workout-related content while watching workout-related content. According to an embodiment, the home gym service may be defined as a service that displays workout-related content on the screen and at the same time provides at least one of the user's health information and the user's workout image.

According to an embodiment, when providing a home gym service 412 to the user, the electronic device 101 may display the user's health information and the user's workout image together while playing back workout-related content based on the video playback application 450 (e.g., a third-party application, a multiplayer program, and/or a multiplayer). The electronic device 101 may provide the user with workout-related content, health information about the user, and a workout image, and the user can perform home training while identifying his or her health information and his or her workout posture.

According to an embodiment, the electronic device 101 may include the video playback application 450 (e.g., a third-party application, a multiplayer program, and/or a multiplayer) for displaying workout-related content, a home gym application 410 for providing a home gym service 412 to the user, a health application 420 for acquiring the user's health information, and/or a mirroring application 430 for the same output of a user interface 411 displayed on the display module 160 of the electronic device 101 through the display device 320.

According to an embodiment, the electronic device 101 may execute the home gym application 410 for providing the home gym service 412 to the user and may activate the home gym application 410 in the background. According to an embodiment, the electronic device 101 may execute the health application 420 in response to the execution of the home gym application 410. When the home gym application 410 is activated, the processor 120 may identify whether a workout-related function has been executed in the video playback application 450 or whether workout-related content has been played. The home gym application 410 may determine the configuration information by the user. The configuration information may include information as shown in (Table 1) below.

TABLE 1

| name | type | mandatory |
|---|---|---|
| Package_ name | string | O |
| hr | boolean | X |
| Calorie | boolean | X |
| Duration | boolean | X |
| Preview | boolean | X |
| View_type | int | X |

For example, the Package_name may be provided in the form of a string and may indicate whether the workout-related content is executed in the background state or foreground state in the video playback application 450 (e.g., a third-party app). According to an embodiment, the home gym application 410 may determine whether to execute workout-related content based on the configuration information. According to an embodiment, the video playback application 450 may determine whether to play workout-related content through the health program service 451 and report whether the workout-related content is played to the home gym application 410. The home gym application 410 may determine whether to execute workout-related content based on the information reported from the video playback application 450. The home gym application 410 may be executed in the same way as the package state of the workout-related content. For example, heart rate/calorie/ duration is provided in a boolean format, and the home gym application 410 may determine whether to provide the user's heart rate information, calorie information, and/or workout time information together with the workout-related content. With reference to Table 1, the home gym application 410 may not provide all of the heart rate information, the calorie information, and/or the workout time information when displaying workout-related content. For example, the preview may indicate whether to provide a user's workout image (e.g., a preview image) photographed using the camera module 180. The View_type may indicate information about the screen configuration when the workout image is provided to the user. For example, the View_type may display the workout-related content and the user's workout image in the same proportion and half-and-half on the screen, or the user's workout image may be laid out based on the workout-related content and be displayed over the workout-related content.

According to an embodiment, when a workout-related function is executed, the video playback application 450 may transmit workout-related information indicating that the workout-related function has been executed to the home gym application 410. For example, the video playback application 450 may broadcast that a workout-related function has been executed. The workout-related information may include code information such as Table 2.

TABLE 2

| |
|---|
| < action android:name="com.samsung.android.app.homegym.FITNESS" /> |

According to an embodiment, when the home gym application 410 receives workout-related information from the video playback application 450, it may identify that the workout-related function has been executed based on the video playback application 450.

According to an embodiment, the video playback application 450 may generate workout-related metadata when workout-related content is played. Workout-related metadata may include code information such as Table 3.

TABLE 3

| |
|---|
| METADATA_KEY_GENRE = "com.samsung.android.app.homegym.FITNESS" |

According to an embodiment, the video playback application 450 may add metadata "com.samsung.android.app.homegym.FITNESS" to the METADATA_KEY_GENRE when playing workout-related content. The home gym application 410 may acquire metadata information from the video playback application 450 when workout-related content is played through the video playback application 450 and identify the metadata information included in the METADATA_KEY_GENRE.

According to various embodiments, the electronic device 101 may identify workout-related information and/or metadata through the video playback application 450 while the home gym application 410 is active, and the video playback application 450 may determine whether workout-related content is being played.

According to an embodiment, the electronic device 101 may also execute the health application 420 in response to the execution of the home gym application 410. The home gym application 410 may be interlocked with the health application 420, and through the health application 420, the user's health information (e.g., the heart rate information, the movement information, the calorie information) may be acquired from an external electronic device (e.g., the wearable device 310). According to an embodiment, the home gym application 410 and the health application 420 may perform inter-process communication (IPC) interworking with each other. For example, when interlocking with IPC, the home gym application 410 may operate as a client, and the health application 420 may operate as a host. The home gym application 410 (e.g., the client) may request the workout tracking service 421 from the health application 420 (e.g., the host), and the health application 420 may provide information related to the workout tracking service 421 to the home gym application 410. The home gym application 410 and the health application 420 may form an environment in which messages are exchanged with each other.

According to an embodiment, the home gym application 410 may request the health information of the user from the health application 420. In response to the request, the health application 420 may execute the workout tracking service 421. For example, the health application 420 may acquire the health information of the user using the wearable device 310 connected to the electronic device 101 and provide the acquired health information to the home gym application 410. The wearable device 310 may measure the health information of the user using the health application 461. The wearable device 310 may be mounted on the user's wrist, and a sensor module (e.g., the sensor module 313 of FIG. 3) may be disposed in response to the vascular position of the user's wrist. The wearable device 310 may execute the health application 461 to measure the health information of the user and provide the measured health information to the health application 420. The health application 420 may provide the user's health information measured through the wearable device 310 to the home gym application 410.

According to an embodiment, when executing the workout tracking service 421, the health application 420 may photograph the user's workout scene using the camera module 180 of the electronic device 101. For example, the user may place the camera module 180 of the electronic device 101 to focus on himself or herself during home training and control the electronic device 101 so that the electronic device 101 photographs his or her workout scene. The health application 420 may acquire a user's workout scene photographed using the camera module 180 and may provide image information on which the user's workout scene is photographed to the home gym application 410. According to an embodiment, the home gym application 410 may directly access the camera module 180 while playing video related content through the video playback application 450 and may use the camera module 180 to acquire a user's workout scene.

According to an embodiment, the home gym application 410 may acquire the user's health information and the user's workout scene image information from the health application 420 and configure the user interface 411 based on the health information and the image information. For example, the home gym application 410 may determine whether to include the health information and the image information in the user interface 411, or if so, in which area to dispose it. For example, the configuration information described in above Table 1 may include configuration information such as whether to include the health information and the image information in the user interface 411, or if so, in which area to dispose it, and the home gym application 410 may configure the user interface 411 based on the configuration information.

According to an embodiment, the home gym application 410 may display the user interface 411 at the display unit 462 of the display device 320 that communicates with the electronic device 101 through the mirroring application 430. For example, the display device 320 may include a display unit 462 (e.g., the display module 323 of FIG. 3) and display a user interface 411 based on the display unit 462.

According to various example embodiments, an electronic device may comprise: a communication module comprising communication circuitry configured to communicate with at least one external electronic device; a memory for storing at least one app; and a processor operatively connected to the communication module and the memory. The processor may be configured to: activate a workout management app (e.g., home gym app) stored in the memory; in response to the execution of the at least one app, identify whether a workout-related content has been executed based on the activated workout management app; display an object for execution of a training program through the workout management app based on the workout-related content being executed; in response to an input on the object, make an automatic connection with the at least one external electronic device through the communication module; configure, based on at least one workout-related information acquired from the at least one external electronic device, a training program screen into which the workout-related content and the workout-related information are integrated; and control the external electronic device to display the training program screen.

According to an example embodiment, the processor may be configured to at least partially activate the workout management app in the background state.

According to an example embodiment, the processor may be configured to: identify the declaration information according to the execution of the workout-related function based on the workout management app and identify that the workout-related content has been executed based on the identified declaration information.

According to an example embodiment, the processor may be configured to: identify the metadata according to playback of workout-related content based on the workout management app and identify that the workout-related content has been executed based on the identified metadata.

According to an embodiment, the at least one external electronic device may include: a wearable device including circuitry configured to acquire biometric information and a display device including a display configured to display a workout image of a user, wherein the workout-related information may include biometric information and a workout image of the user.

According to an example embodiment, the processor may be configured to acquire biometric information of a user measured using the wearable device from the wearable device.

According to an example embodiment, the biometric information of the user may include at least one of a heart rate, a heart rate variability (HRV), a calorie consumption, an oxygen saturation $SpO_2$, a blood pressure (BP), a fatigue, a stress, a blood sugar, a body water, an electrocardiogram (ECG), an electrodermal activity (EDA), a bioelectrical impedance analysis (BIA), and a workout elapsed time.

The electronic device according to an example embodiment may further include: a camera module including a camera configured to photograph the user's workout image, and the processor may be configured to control the camera module to photograph the user's workout scene in a real time or according to a specified time interval and acquire the user's workout image using the camera module.

According to an example embodiment, the processor may be configured to: activate a health management app (e.g., a health app) configured to acquire at least one workout-related information, and based on the health management app, the processor may configured to at least partially control the wearable device included in the at least one external electronic device.

According to an example embodiment, the processor may be configured to: perform inter-process communication (IPC) interworking between the workout management app and the health management app, acquire the messenger information of another party, and transmit the message between the workout management app and the health management app based on the acquired messenger information.

According to an example embodiment, the processor may be configured to: activate a mirroring app for displaying the training program screen, and may at least partially control a display device included in the at least one external electronic device based on the mirroring app.

Figure 5:
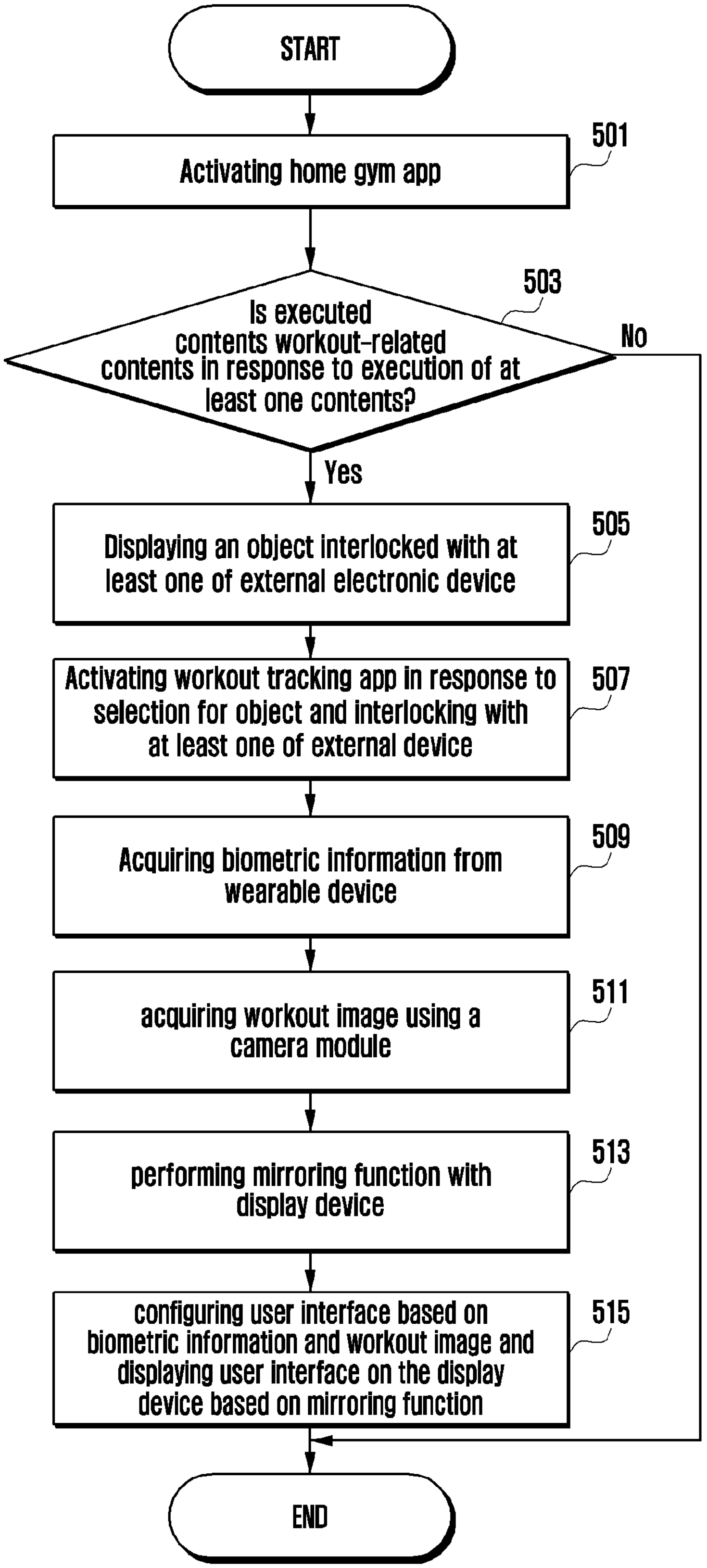
FIG. 5 is a flowchart illustrating an example method of displaying a workout image according to various embodiments.

FIG. 5 is a flowchart illustrating an example method of displaying a workout image according to various embodiments.

According to various embodiments, the electronic device (e.g., the electronic device 101 of FIG. 1) may be operatively connected to at least one external electronic device (e.g., the wearable device 310 of FIG. 3 and/or the display device 320 of FIG. 3) and may at least partially control the at least one external electronic device. According to an embodiment, the electronic device 101 may provide a home gym service to a user who wants home training. Home training may refer to a method in which the user performs a workout alone indoors, and the electronic device 101 may provide a home gym service to improve the workout effect of the user through home training. According to an embodiment, the home gym service may refer, for example, to a service that provides at least one of the user's health information and the user's workout image together based on workout-related content. In displaying workout-related content through the display device 320, the electronic device 101 may display the health information of the user acquired using the wearable device 310. The electronic device 101 may photograph a user's workout scene using a camera module (e.g., the camera module 180 of FIG. 1) and display the photographed image together with the workout-related content. The electronic device 101 may perform a home gym service that provides a home gym service that provides a user with workout-related content including a user's health information and a workout scene.

In operation 501, the processor of the electronic device 101 (e.g., the processor 120 of FIG. 3) may activate a home gym application (e.g., the home gym application 410 of FIG. 4) for providing a home gym service to a user. For example, the processor 120 may activate the home gym application 410 in the background. When the home gym application 410 is activated, the home gym service may be performed.

In operation 503, the processor 120 may identify whether the executed content is content related to workout in response to the execution of at least one content. The electronic device 101 may store at least one application in a memory (e.g., the memory 130 of FIG. 1). At least one application may include a video playback application (e.g., the video playback application 450 of FIG. 4).

In operation 503, the processor 120 may identify whether a workout-related function is being executed or whether workout-related content is being played using the video playback application 450. For example, the video playback application 450 may declare that the workout-related function has been executed when the workout-related function is executed, and the processor 120 may identify that the workout-related function has been executed based on the declaration. For example, the video playback application 450 may generate workout-related metadata when workout-related content is played and may report the generated workout-related metadata to the home gym application 410. The processor 120 may identify that the workout-related content has been executed based on the workout-related metadata reported from the video playback application 450 through the home gym application 410.

According to an embodiment, the processor 120 may determine whether the running content is workout-related content based on the declaration information of the workout-related function and the metadata of the workout-related content.

Once the execution of the workout-related content is identified in operation 503, the processor 120 in operation 505 may display an object (e.g., an icon, a ticker, and/or a pop-up message) for interworking with at least one external electronic device (e.g., the wearable device 310 of FIG. 3, the display device 320 of FIG. 3). For example, the object may include a notification message for providing a home gym service to the user. For example, the processor 120 may display the object so that it is laid out on the screen currently being displayed. The processor 120 may apply a highlight effect (e.g., to emphasize the object, adjust brightness, color, and/or density) to indicate that the object has been generated.

In operation 507, the processor 120 may activate a workout tracking app (e.g., the health application 420 of FIG. 4) in response to a selection (e.g., a user's touch input) for the object, and may be interworked with at least one external electronic device. The processor 120 may perform wireless communication with at least one of the wearable devices 310 and/or the display device 320 through a communication module (e.g., the communication module 190 of FIG. 3).

In operation 509, the processor 120 may acquire biometric information of the user from the wearable device 310. For example, the wearable device 310 may be worn in at least partial contact with the user's body and may measure and acquire the user's biometric information. For example, the biometric information of the user that the processor 120 may acquire from the wearable device 310 may include at least one of a heart rate (HR), a heart rate variability (HRV), a calorie consumption, an oxygen saturation (($SpO_2$), a blood pressure (BP), a fatigue, a stress, a blood sugar, a body hydration, an electrocardiogram (ECG), an electrodermal activity (EDA), and a bioelectrical impedance analysis (BIA). For example, the electrodermal activity (EDA) may include galvanic skin response (GSR) information. According to an embodiment, the wearable device 310 may include a wearable watch worn on the user's wrist. According to an embodiment, the processor 120 may request the user's biometric information from the wearable device 310 based on the workout tracking app, and in response to the request, the wearable device 310 may provide the user's biometric information to the electronic device 101. Operation 509 may be performed according to the user's configurations for the home gym service.

In operation 511, the processor 120 may photograph a user's workout scene and acquire a workout image using a camera module (e.g., camera module 180 of FIG. 3, a camera device disposed in the electronic device 101). The electronic device 101 may be disposed in a position where the user's workout scene can be photographed and may photograph the user's workout scene in real time or for a predetermined time by activating the camera module 180. Whether to perform operation 511 may be determined according to the user's configurations for the home gym service.

In operation 513, the processor 120 may perform a mirroring function with the display device 320. For example, the processor 120 may execute a mirroring app (e.g., the mirroring app 430 of FIG. 4) for performing a mirroring function, and may perform a mirroring function for the display device 320 based on the mirroring app. According to an embodiment, the processor 120 may perform a mirroring function, so that the screen being displayed through the display module (e.g., the display module 160 of FIG. 1) is displayed at the same screen in the display device 320. Operation 513 may be performed according to the user's configurations for the home gym service.

According to an embodiment, operations 509 to 513 may be executed sequentially or substantially simultaneously, and the order of operation may be changed depending on how the user configures. The order of operations 509 to 513 is not limited.

In operation 515, the processor 120 may include a user interface (e.g., the user interface 411 of FIG. 4) based on the biometric information acquired from the wearable device 310 and the workout image photographed using the camera module 180. The processor 120 may display the user interface 411 on the display device 320 by performing a mirroring function for the display device 320.

According to an embodiment, the electronic device 101 may provide a home gym service to the user, and through the display device 320, in displaying workout-related content, the user's health information and/or the user's workout scene may be displayed together. For example, the electronic device 101 may acquire the user's health information from the wearable device 310 and may photograph the user's workout scene using the camera module 180. The electronic device 101 may configure a user interface corresponding to the home gym service based on the user's health information and the user's workout scene and may perform a mirroring function for the display device 320 so that the user interface is displayed through the display device 320. The electronic device 101 may perform a home gym service to provide a home training user with his or her health information (e.g., a heart rate, a calorie consumption) and his or her workout posture while watching workout-related content. The home gym service can provide users with the ability to improve their workout efficiency according to home training. Users can maximize and/or improve the effect of workout according to home training.

Figure 6:
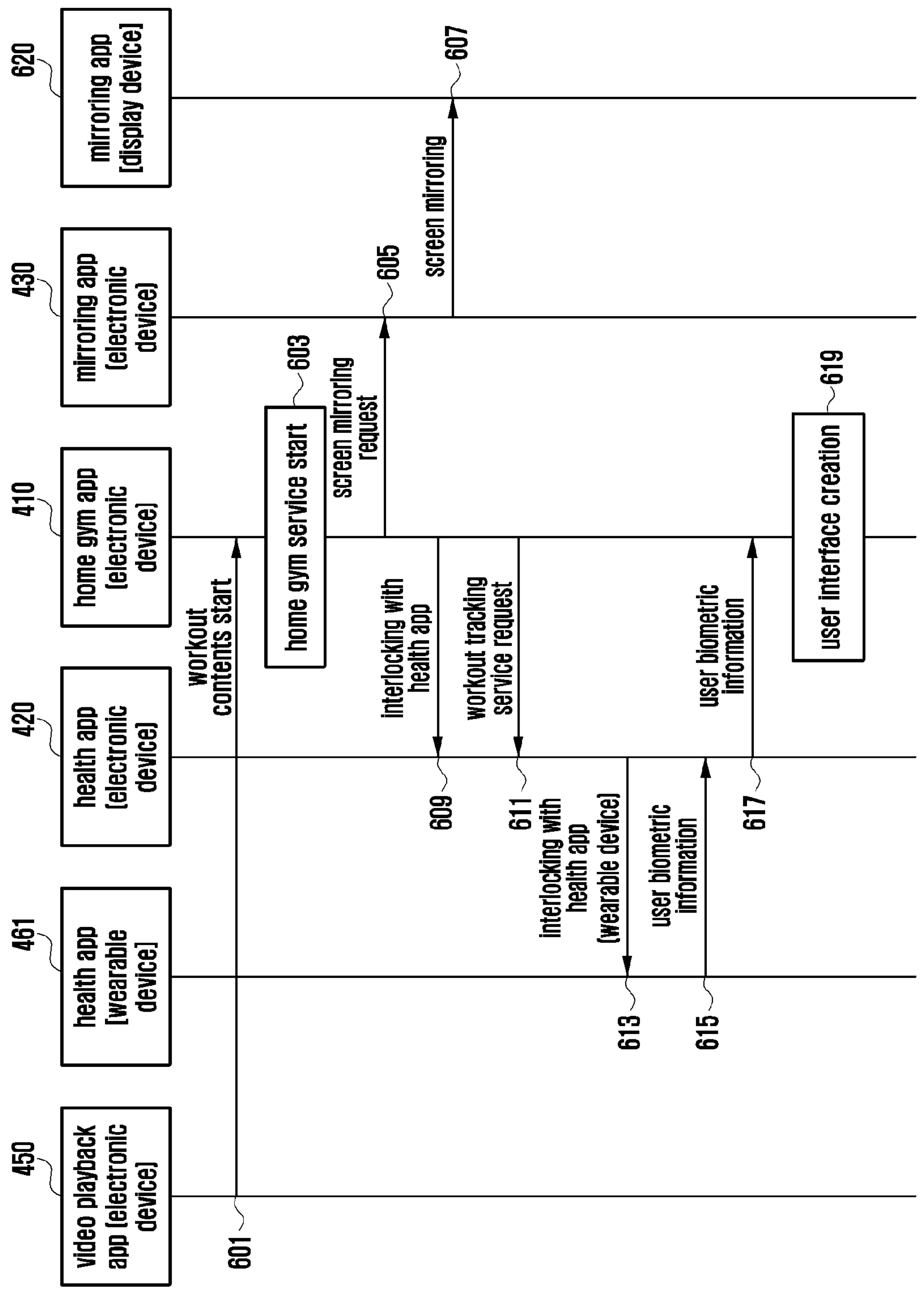
FIG. 6 is a signal flow diagram illustrating an example method of providing a home gym service to a user in an electronic device and an external electronic device according to various embodiments.

FIG. 6 is a signal flow diagram illustrating an example method of providing a home gym service to a user in an electronic device (e.g., the electronic device 101 of FIG. 1) and an external electronic device (e.g., the wearable device 310 of FIG. 3, the display device 320 of FIG. 3) according to various embodiments. FIG. 6 illustrates an example operation of transmitting and receiving data between at least one application installed in the electronic device 101 and at least one application installed in at least one external electronic device (e.g., the wearable device 310, the display device 320).

According to an embodiment, the electronic device 101 may include a home gym application (e.g., the home gym application 410 of FIG. 4) for providing a home gym service to a user, a health application (e.g., the health application 420 of FIG. 4) for acquiring the user's health information, a mirroring application (e.g., the mirroring application 430 of FIG. 4) for displaying the same screen as the screen of the electronic device 101, and/or a video playback application (e.g., the video playback application 450 and the third party app of FIG. 4) for playing back an image may be stored in a memory (e.g., the memory 130 of FIG. 1) and each application may be executed. According to an embodiment, the wearable device 310 may respond to a request from the electronic device 101 to execute a health application 461 to provide biometric information of the user. According to an embodiment, the display device 320 may execute the mirroring application 620 for performing the mirroring function in response to the request of the electronic device 101.

According to an embodiment, the electronic device 101 may execute the home gym application 410 in providing a home gym service to the user, and the home gym application 410 may be activated. For example, the home gym application 410 may remain running in the background.

In operation 601, the electronic device 101 may play back workout-related content using the video playback application 450. The electronic device 101 may identify whether the workout-related content is played based on the declaration information and metadata corresponding to the video playback application 450 through the running home gym application 410. For example, the video playback application 450 may generate workout-related metadata when workout-related content is played and may report the generated workout-related metadata to the home gym application 410. The home gym application 410 may identify that the workout-related content has been executed based on the reported workout-related metadata. According to an embodiment, the video playback application 450 may declare that the workout-related function has been executed when the workout-related function is executed, and the home gym application 410 may identify that the workout-related function has been executed based on the declaration information.

In operation 603, the home gym application 410 may identify the playback of workout-related content and start the home gym service. According to an embodiment, the state in which the home gym application 410 is activated in the background may be defined as the start of the home gym service. According to an embodiment, when the home gym service is executed, the electronic device 101 may perform wireless communication with the wearable device 310 and/or the display device 320 and may transmit and receive data to/from each other.

In operation 605, the home gym application 410 may request screen mirroring according to the execution of the mirroring function to the mirroring application 430, and in operation 607, the mirroring application 430 may request screen mirroring to the mirroring application 620 running in the display device 320. For example, screen mirroring may be defined as a function that displays identically the screen being displayed through the display module 160 of the electronic device 101 at the display device 320. According to an embodiment, in the case of interlocking each other, when the screen of the electronic device 101 is changed based on the mirroring function in the electronic device 101 and the display device 320, the screen of the display device 320 may also be changed in the same way as the screen of the electronic device 101. According to an embodiment, compared to the user interface displayed on the screen of the electronic device 101, the display device 320 may display at least a partially adjusted user interface based on the size of the screen, the ratio of the screen, the resolution, and/or the number of pixels.

In operation 609, the home gym application 410 may be interlocked with the health application 420, and in operation 611, a workout tracking service may be requested.

In operation 613, the health application 420 may request the user's biometric information from the health application 461 running on the wearable device 310. For example, the wearable device 310 may be mounted to at least partially contact the user's body and may measure the user's biometric information (e.g., a heart rate, a calorie consumption). In operation 615, the health application 461 of the wearable device 310 may provide the user's biometric information to the health application 420 of the electronic device 101.

In operation 617, the health application 420 may provide the home gym application 410 with the user's biometric information acquired from the wearable device 310.

In operation 619, the home gym application 410 may generate a user interface corresponding to the home gym service. For example, the home gym application 410 may generate a user interface to display workout-related content and the user's biometric information acquired from the wearable device 310 together. According to an embodiment, the home gym application 410 may use a camera module of the electronic device 101 (e.g., the camera module 180 of FIG. 1) to photograph a user's workout scene and acquire a user's workout image. The home gym application 410 may generate a user interface based on workout-related content, the user's biometric information, and/or the user's workout image.

Figure 7A:
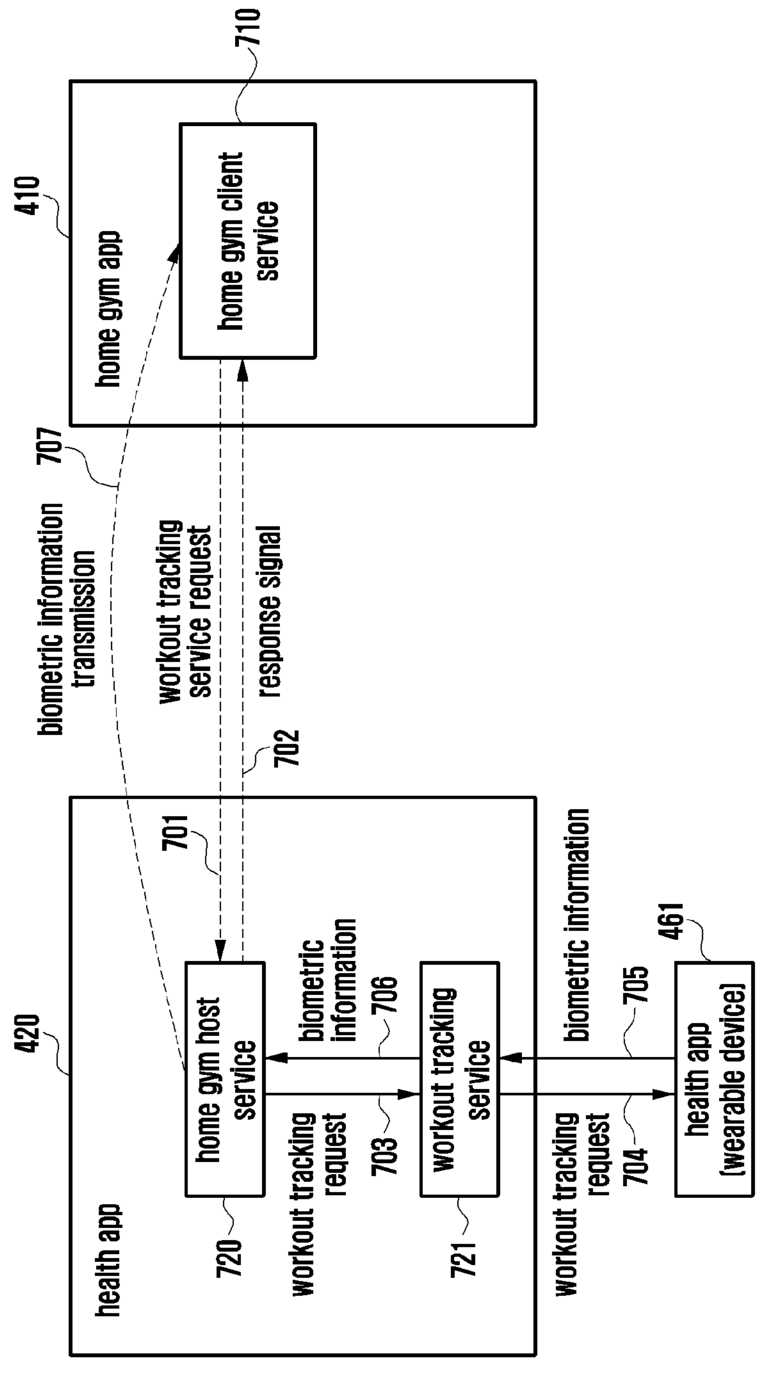
FIG. 7A is a diagram illustrating an example operation of exchanging information between a home gym app and a health app installed in an electronic device according to various embodiments.

FIG. 7A is a diagram illustrating an example operation of exchanging information between a home gym app and a health app installed in an electronic device according to various embodiments of the present disclosure.

According to an embodiment, the electronic device (e.g., the electronic device 101 of FIG. 1) may perform a home gym application (e.g., the home gym application 410 of FIG. 4) to provide a home gym service to the user and/or a health application (e.g., the health application 420 of FIG. 4) to acquire biometric information. The home gym application 410 and the health application 420 may be inter-process communication (IPC) interworking with each other. For example, when interlocking with IPC, the home gym application 410 may perform a home gym client service 710 corresponding to a client, and the health application 420 may perform a home gym host service 720 corresponding to a host. When the IPC is interlocked, data may be shared by transmitting and receiving messages between the home gym client service 710 and the home gym host service 720.

With reference to FIG. 7A, in operation 701, the home gym client service 710 may request a workout tracking service to the home gym host service 720, and in operation 702, the home gym host service 720 may transmit a response signal to the home gym client service 710.

In operation 703, the home gym host service 720 may perform a workout tracking request to the workout tracking service 721. In operation 704, the workout tracking service 721 may transmit a workout tracking request signal to the health application 461 of the wearable device (e.g., the wearable device 310 of FIG. 3). In operation 705, the health application 461 of the wearable device 310 may provide the user's biometric information to the workout tracking service 721 in response to the request. In operation 706, the workout tracking service 721 may transmit the user's biometric information to the home gym host service 720.

In operation 707, the home gym host service 720 may provide the home gym client service 710 with the user's biometric information acquired from the health application 461 of the wearable device 310.

According to an embodiment, the home gym application 410 and the health application 420 may maintain an IPC interlocking state and may transmit and receive messages to/from each other.

Figure 7B:
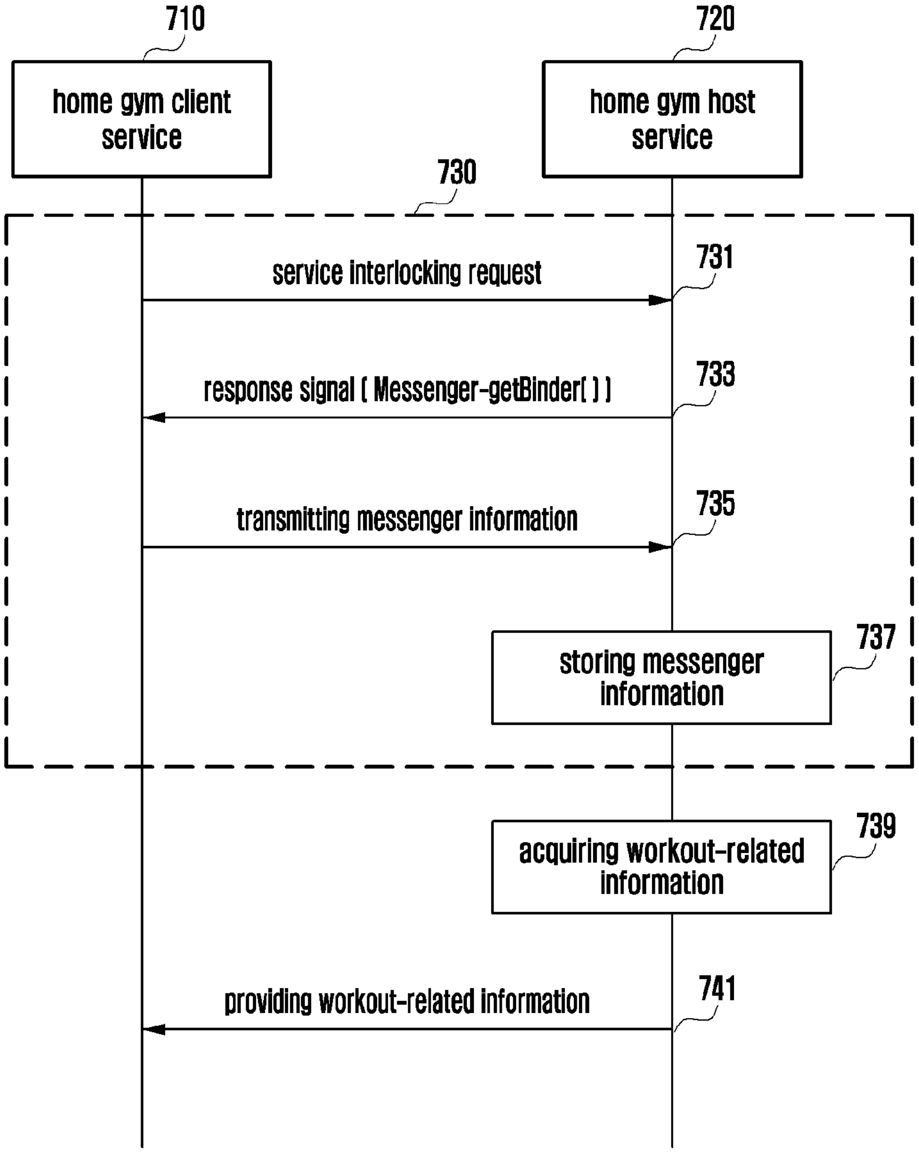
FIG. 7B is a signal flow diagram illustrating an example operation between a home gym host service and a home gym client service according to various embodiments.

FIG. 7B is a signal flow diagram illustrating an example operation between a home gym host service and a home gym client service according to various embodiments of the present disclosure.

According to an embodiment, the electronic device (e.g., the electronic device 101 of FIG. 1) may perform a home gym application (e.g., the home gym application 410 of FIG. 4) to provide a home gym service to the user and/or a health application (e.g., the health application 420 of FIG. 4) to acquire biometric information. The home gym application 410 and the health application 420 may be inter-process communication (IPC) interworking with each other. The home gym application 410 may perform the home gym client service 710, and the health application 420 may perform the home gym host service 720.

FIG. 7B illustrates the process 730 in which IPC interlocking is established between the home gym client service 710 and the home gym host service 720 and the operation of transmitting data. In operation 731, the home gym client service 710 may request service interlocking (e.g., IPC interlocking) to the home gym host service 720 to provide a home gym service to the user. For example, the home gym client service 710 may request a binding to the home gym host service 720. In operation 733, the home gym host service 720 may transmit a response signal (e.g., a messenger-getBinder[ ] signal, a messenger instance to the home gym host service 720) to the home gym client service 710. In operation 735, the home gym client service 710 may transmit messenger information (e.g., a messenger instance for the home gym client service 710) to the home gym host service 720. For example, the messenger information may include information related to the transmission of messages to be transmitted and received when the IPC is interworked. In operation 737, the home gym host service 720 may store messenger information. The home gym client service 710 may acquire a messenger instance for the home gym host service 720, and the home gym host service 720 may acquire a messenger instance for the home gym client service 710. According to an embodiment, when performing operations 730 of operation 731 to operation 737, messenger instances for each other may be acquired, and IPC interworking may be established between the home gym client service 710 and the home gym host service 720.

In operation 739, the home gym host service 720 may acquire workout-related information (e.g., the biometric information of the user related to workout) for a user from the wearable device (e.g., the wearable device 310 of FIG. 3) in the state of having an IPC interworking with the home gym client service 710. In operation 741, the home gym host service 720 may provide the workout-related information in the form of a message to the home gym client service 710.

Figure 8:
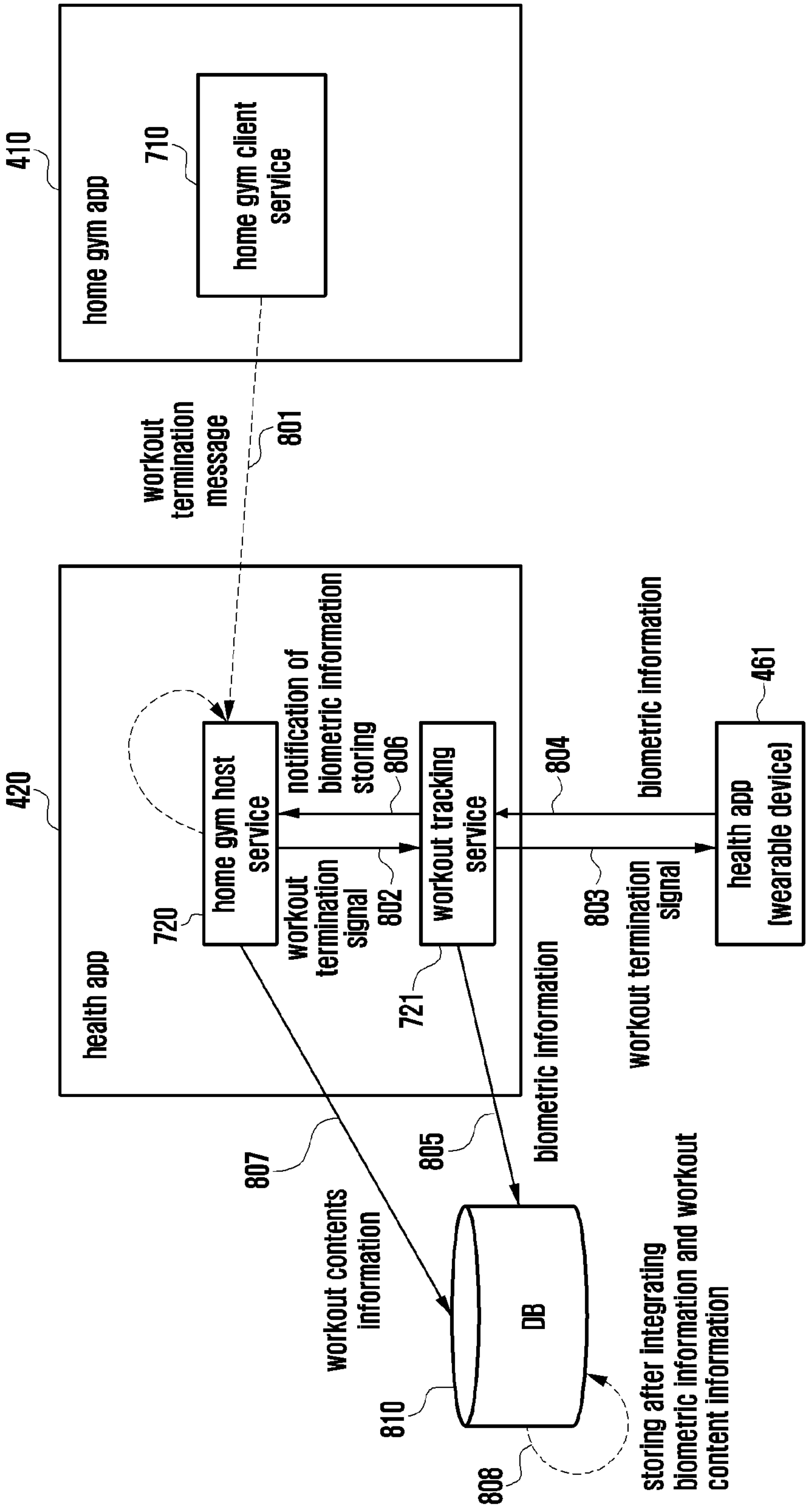
FIG. 8 is a diagram illustrating an example operation of exchanging information between the home gym app and the health app when a home gym service is terminated according to various embodiments.

FIG. 8 is a diagram illustrating an example operation of exchanging information between the home gym app and the health app when a home gym service is terminated according to various embodiments.

According to an embodiment, the electronic device (e.g., the electronic device 101 of FIG. 1) may perform a home gym application (e.g., the home gym application 410 of FIG. 4) to provide a home gym service to the user and/or a health application (e.g., the health application 420 of FIG. 4) to acquire biometric information. The home gym application 410 and the health application 420 may be inter-process communication (IPC) interworking with each other. For example, when interworking with IPC, the home gym application 410 may perform a home gym client service 710 corresponding to a client, and the health application 420 may perform a home gym host service 720 corresponding to a host. When the IPC is interworked, data may be shared by transmitting and receiving messages between the home gym client service 710 and the home gym host service 720.

With reference to FIG. 8, in operation 801, the home gym client service 710 may transmit a workout termination message to the home gym host service 720. For example, when the user terminates the home gym service, the home gym client service 710 may transmit a workout termination message to the home gym host service 720.

In operation 802, the home gym host service 720 may transmit a workout termination signal to the workout tracking service 721, and in operation 803, the workout tracking service 721 may transmit the workout termination signal to the health application 461 of the wearable device 310 (e.g., the wearable device 310 of FIG. 3). In operation 804, the health application 461 of the wearable device 310 may respond to the request and provide the last measured user's biometric information to the workout tracking service 721. In operation 805, the workout tracking service 721 may reflect the biometric information of the user last measured on the database 810 stored in the memory 130. In operation 806, the workout tracking service 721 may notify the home gym host service 720 that the biometric information of the user last measured has been stored in the database (DB) 810.

In operation 807, the home gym host service 720 may transmit information (e.g., playback video information, playback image information) about workout-related content to the database (DB) 810. In operation 808, the database 810 may integrate and store information on the user's biometric information and workout-related content provided from the health application 420. According to an embodiment, the processor 120 of the electronic device 101 may configure and display a user interface based on the database 810 stored in the memory 130 when the home gym service is terminated. When the home gym service is terminated, the user may identify the integrated results of home training by the home gym service. For example, the user may intuitively identify the amount of heart rate change due to home training, calorie consumption, and/or time information of performing home training.

Figure 9:
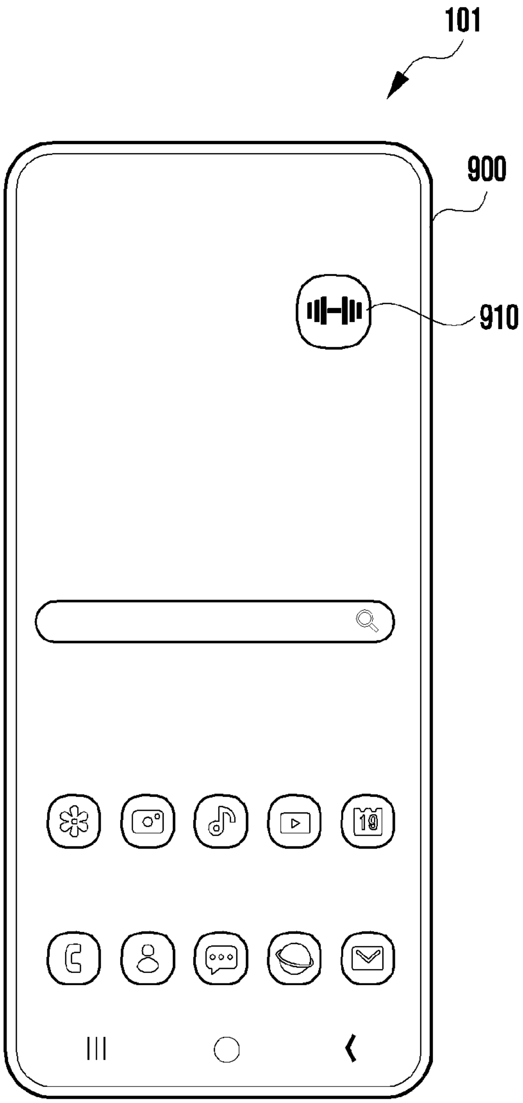
FIG. 9 is a diagram illustrating a screen displaying an object for interworking with an external electronic device in an electronic device according to various embodiments.

FIG. 9 is a diagram illustrating an example screen displaying an object for interworking with an external electronic device in an electronic device according to various embodiments.

With reference to FIG. 9, an electronic device (e.g., the electronic device 101 of FIG. 1) illustrates a screen 900 that provides an object 910 for starting a home gym service. For example, object 910 may include various types of graphical user interface (GUI), such as an icon, a ticker, and/or a pop-up message. The object 910 may be displayed through a display module of the electronic device 101 (e.g., the display module 160 of FIG. 1) or a wearable device interlocked to the electronic device 101 (e.g., the wearable device 310 of FIG. 3).

According to an embodiment, the processor of the electronic device 101 (e.g., the processor 120 of FIG. 1) may execute a home gym application (e.g., the home gym application 410 of FIG. 4) for providing a home gym service to a user. For example, the processor 120 may execute the home gym application 410 in the background, and the home gym application 410 may be at least partially activated.

According to an embodiment, the processor 120 may respond to the execution of at least one content to determine whether the executed content is content related to workout. The electronic device 101 may store at least one application in a memory (e.g., the memory 130 of FIG. 1). At least one application may include a video playback application (e.g., the video playback application 450 of FIG. 4). The processor 120 may use the video playback application 450 to determine whether a workout-related function is being executed, or whether workout-related content is being played. For example, the video playback application 450 may declare that the workout-related function has been executed when the workout-related function is executed, and the processor 120 may identify that the workout-related function has been executed based on the declaration. For example, the video playback application 450 may generate workout-related metadata when workout-related content is played, and the processor 120 may identify that workout-related content has been executed based on the metadata. According to an embodiment, the processor 120 may determine whether the running content is workout-related content based on the declaration information of the workout-related function and the metadata of the workout-related content.

With reference to FIG. 9, the processor 120 may detect the execution of a workout-related function or playback of workout-related content, and in response to the detection, an object 910 for starting a home gym service may be displayed on the screen 900. For example, the object 910 may be laid out on the screen 900 and displayed on the uppermost layer. According to an embodiment, the processor 120 may apply a highlight effect (e.g., adjusting brightness, color, or intensity to emphasize the object) to the object 910.

Figure 10A:
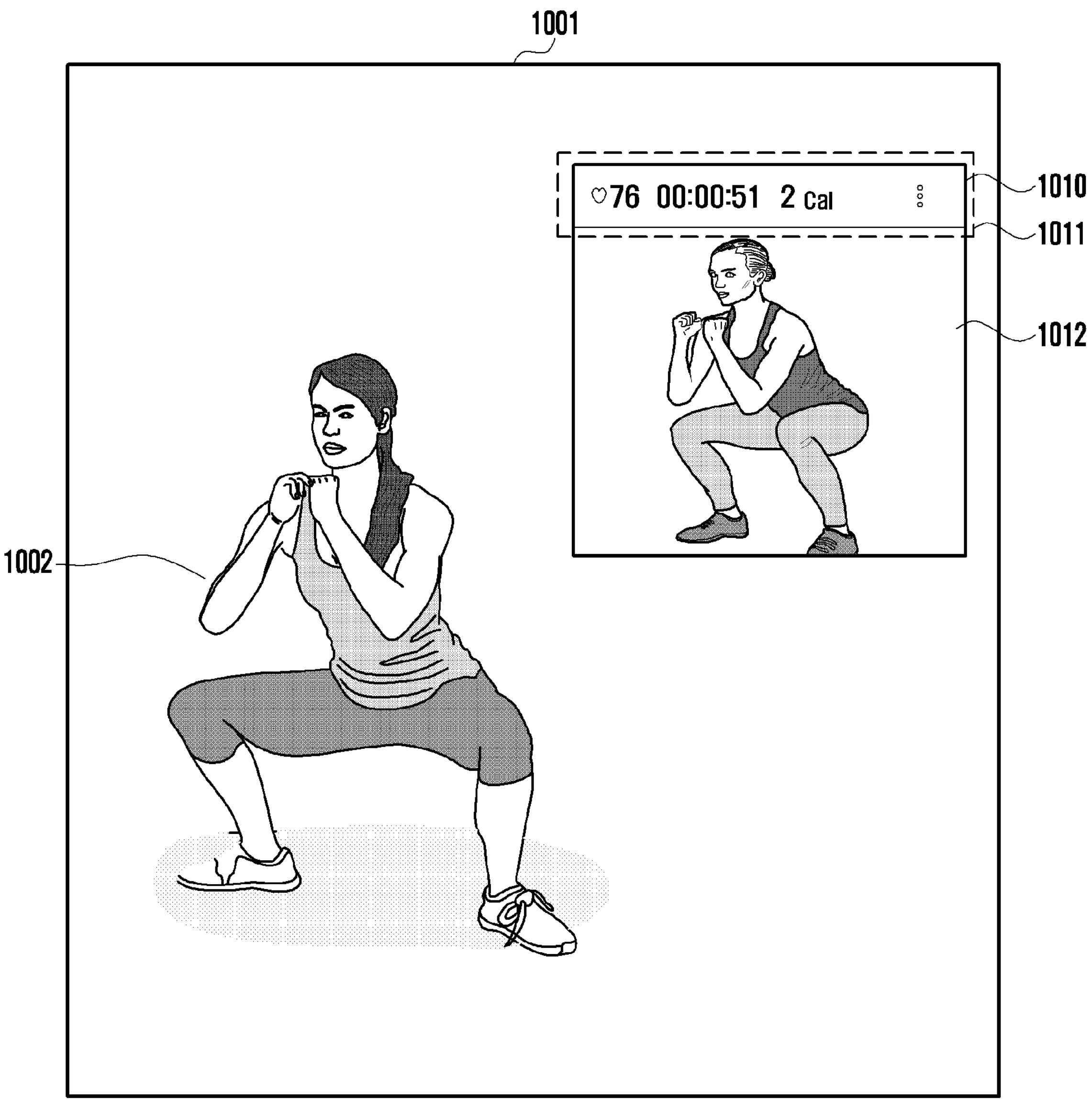
FIG. 10A is a diagram illustrating a screen displaying the user's biometric information and the user's workout state when a home gym service is provided according to various embodiments.

FIG. 10A is a diagram illustrating an example screen displaying the user's biometric information and the user's workout state when a home gym service is provided according to various embodiments.

According to an embodiment, an electronic device (e.g., the electronic device 101 of FIG. 1) may provide a home gym service to a user who wants home training. The home gym service may be defined as a service that provides at least one of the user's health information and the user's workout image together based on workout-related content. FIG. 10*a* illustrates a user interface by a home gym service.

According to an embodiment, the electronic device 101 may be operatively connected to at least one external electronic device (e.g., the wearable device 310 of FIG. 3 and/or the display device 320 of FIG. 3) and the at least one external electronic device may be controlled at least partially. According to an embodiment, the electronic device 101 may acquire biometric information of the user from the wearable device 310. The electronic device 101 may use a camera module (e.g., the camera module 180 of FIG. 1) to photograph a user's workout scene and acquire a workout image. According to an embodiment, when providing a home gym service, the electronic device 101 may configure a user interface based on the user's biometric information and the user's workout image, and through the display device 320, the display device 320 may be at least partially controlled so that the user interface is displayed.

With reference to FIG. 10A, when providing a home gym service, a user interface 1001 displayed through the display device 320 is shown. In displaying workout-related content 1002, the user interface 1001 may additionally add a sub window 1010. For example, the sub window 1010 may include the user's biometric information 1011 acquired from the wearable device 310 and the user's workout image 1012 photographed using the camera module 180. The user's biometric information 1011 may include at least one of the heart rate (HR), the workout elapsed time, and/or the calorie consumption of the user performing home training. The user's workout image 1012 may display a user's workout image photographed using the camera module 180 in real time. According to an embodiment, the electronic device 101 may measure the amount of change in the user's biometric information in real time according to the playback of workout-related content and may update the information of the user interface 1001.

According to an embodiment, the electronic device 101 may display the user's biometric information and the user's workout image together while playing workout-related content by the home gym service. While doing home training, users may intuitively identify their physical changes and workout posture.

Figure 10B:
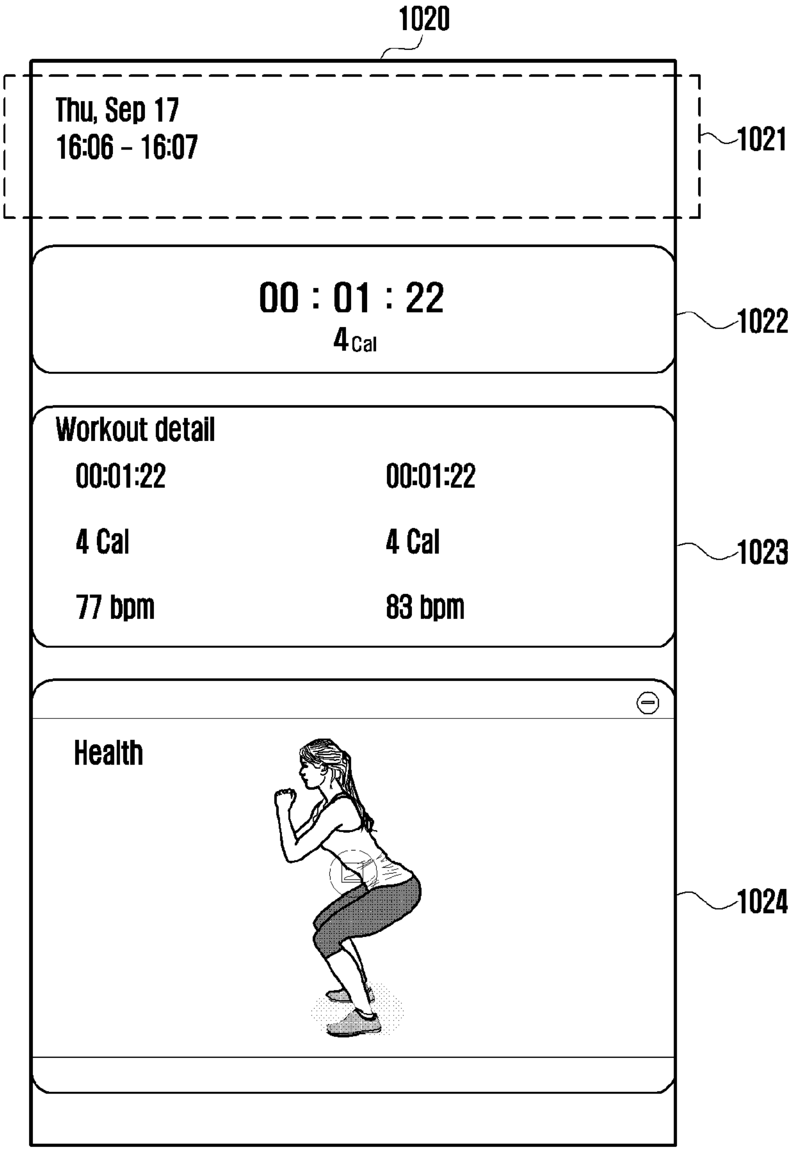
FIG. 10B is a diagram illustrating a screen for recording the results of the user's home training when the home gym service is terminated according to various embodiments.

FIG. 10B is a diagram illustrating an example screen for recording the results of the user's home training when the home gym service is terminated according to various embodiments.

According to an embodiment, the electronic device (e.g., the electronic device 101 of FIG. 1) may record the workout result of the user using the home gym service when the home gym service is terminated. The processor of the electronic device 101 (e.g., the processor 120 of FIG. 1) may display the user interface 1020 for the home gym service through the display device (e.g., the display device 320 of FIG. 3). FIG. 10*b* may display a user interface 1020 reflecting the workout result of a user when the home gym service is terminated.

With reference to FIG. 10B, the user interface 1020 may include a result of the user's workout when the user terminates home training by the home gym service. For example, the user interface 1020 may include time information 1021 when the user used the home gym service, time information on the time the user actually participated in home training, calorie consumption information 1022 by home training, and home training details 1023 including the user's heart rate information, and/or the user's workout image 1024. According to an embodiment, the electronic device 101 may change the configuration information so that only the information desired by the user is displayed and may adjust the information included in the user interface 1020 based on the configuration information.

A method according to various example embodiments may comprise: activating a workout management app for managing a user's workout; identifying whether workout-related content has been executed based on the activated workout management app in response to the execution of at least one app stored in memory; based on the workout-related content being executed, displaying an object for executing a training program through the workout management app; in response to an input to the object, making an automatic connection with at least one external electronic device; configuring a training program screen into which the workout-related content and workout-related information are integrated based on at least one workout-related information acquired from the at least one external electronic device; and displaying the training program screen through the at least one external electronic device According to an example embodiment, the activating the workout management app may include at least partially activating the workout management app in the background.

According to an example embodiment, the identifying whether the workout-related content has been executed may include: identifying the declaration information according to the execution of the workout-related function based on the workout management app, and identifying that the workout-related content has been executed based on the identified declaration information.

According to an example embodiment, the identifying whether the workout-related content has been executed may include: identifying metadata according to playback of workout-related content based on the workout management app and identifying that the workout-related content has been executed based on the identified metadata.

The method according to an example embodiment may further include: measuring the biometric information of the user using a wearable device for acquiring the biometric information of the user, and acquiring the measured biometric information of the user from the wearable device, wherein the biometric information of the user may include at least one of the heart rate, the calorie consumption, and the workout elapsed time for the user.

The method according to an example embodiment may further include: photographing a user's workout scene in real time or according to a specified time interval using a camera module for photographing a user's workout image and acquiring a user's workout image.

The method according to an example embodiment may further include: activating a health management app (e.g., a health app) for acquiring at least one workout-related information, and at least partially controlling a wearable device included in the at least one external electronic device based on the health management app.

The method according to an example embodiment may further include: performing inter-process communication (IPC) interworking between the workout management app and the health management app, acquiring messenger information of another party, and transmitting a message between the workout management app and the health management app based on the acquired messenger information.

The method according to an example embodiment may further include: activating a mirroring app for displaying the training program screen, and at least partially controlling a display device included in at least one external electronic device based on the mirroring app.

The electronic device according to various embodiments may be one of various types of electronic devices. The electronic devices may include, for example, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. An electronic device comprising:

a communication module comprising communication circuitry configured to communicate with a first external electronic device;

memory storing instructions and at least one app; and at least one processor, comprising processing circuitry, operatively coupled to the communication module and the memory, wherein the instructions, when executed by the at least one processor, individually or collectively, cause the electronic device to:

activate a workout management app stored in the memory, identify whether workout-related content is displayed in response to execution of the at least one app based on the activated workout management app, display an object for executing a training program through the workout management app in response to determining that the workout-related content is displayed, receive at least one workout-related information from the first external electronic device through the communication module in response to an input on the object, configure a training program screen in which the workout-related content and at least one workout-related information are integrated based on receiving the at least one workout-related information from the first external electronic device, and display the training program screen on a display of the electronic device.

2. The electronic device of claim 1, wherein the instructions, when executed by the at least one processor, individually or collectively, cause the electronic device to at least partially activate the workout management app in a background state.

3. The electronic device of claim 1, wherein the instructions, when executed by the at least one processor, individually or collectively, cause the electronic device to:

identify declaration information according to execution of workout-related functions based on the workout management app, and identify that the workout-related contents is displayed based on the identified declaration information.

4. The electronic device of claim 1, wherein the instructions, when executed by the at least one processor individually or collectively, cause the electronic device to:

identify metadata according to playback of work out-related content based on the workout management app, and identify that the workout-related content is displayed based on the identified metadata.

5. The electronic device of claim 1, wherein the instructions, when executed by the at least one processor, individually or collectively, cause the electronic device to:

make an automatic connection with a second external electronic device to display a screen corresponding to the training program screen, and control to display the screen through the second external electronic device, wherein the second external electronic device comprises a display device including a display configured to display the screen.

6. The electronic device of claim 1, wherein the instructions, when executed by the at least one processor, individually or collectively, cause the electronic device to: acquire a user's biometric information from the first external electronic device, wherein the user's biometric information is measured using the first external electronic device, wherein the first external electronic device comprises a wearable device, and wherein the at least one workout-related information comprises the user's biometric information.

7. The electronic device of claim 6, wherein the user's biometric information comprises at least one of a heart rate, a heart rate variability (HRV), a calorie consumption, an oxygen saturation ($S_pO_2$), a blood pressure (BP), a fatigue, a stress, a blood sugar, a body moisture, an electrocardiogram (ECG), an electrodermal activity (EDA), a bioelectrical impedance analysis (BIA), and a workout elapsed time for a user.

8. The electronic device of claim 1, further comprising a camera module including at least one camera configured to photograph a workout image of user, wherein the instructions, when executed by the at least one processor, individually or collectively, cause the electronic device to:

control the camera module to photograph the user's workout scene in real time or according to specified time intervals using the camera module, and acquire the user's workout image.

9. The electronic device of claim 1, wherein the instructions, when executed by the at least one processor, individually or collectively, cause the electronic device to:

activate a health management app for acquiring the at least one workout-related information; and at least partially control the first external electronic device based on the health management app.

10. The electronic device of claim 9, wherein the instructions, when executed by the at least one processor, individually or collectively, cause the electronic device to:

perform inter-process communication (IPC) interworking between the workout management app and the health management app, acquire another user's messenger information, and transmit a message between the workout management app and the health management app based on the acquired messenger information.

11. The electronic device of claim 5, wherein the instructions, when executed by the at least one processor, individually or collectively, cause the electronic devices to:

activate a mirroring app to display the training program screen, and at least partially control the second external electronic device to display the screen corresponding to the training program screen based on the mirroring app.

12. A method comprising:

activating a workout management app for managing a user's workout;

identifying whether workout-related content is displayed in response to execution of at least one app stored in memory based on the activated workout management app;

displaying an object for executing a training program through the workout management app in response to determining that the workout-related content is displayed;

receiving at least one workout-related information from a first external electronic device in response to a user input on the object;

configuring a training program screen in which the workout-related content and the at least one workout-related information are integrated based on receiving the at least one workout-related information from the first external electronic device; and displaying the training program screen on a display of an electronic device.

13. The method of claim 12, wherein activating the workout management app comprises at least partially activating the workout management app in a background state.

14. The method of claim 12, wherein identifying whether the workout-related content is displayed comprises:

identifying declaration information according to execution of workout-related functions based on the workout management app; and identifying that the workout-related content is displayed based on the identified declaration information.

15. The method of claim 12, wherein identifying whether the workout-related content is displayed comprises:

identifying metadata according to playback of workout-related content based on the workout management app; and identifying that the workout-related content is displayed based on the identified metadata.

16. The method of claim 12, further comprising:

measuring a user's biometric information using the first external electronic device; and acquiring the measured user's biometric information from the first external electronicdevice, wherein the first external electronic device comprises a wearable device, wherein the at least one workout-related information comprises the user's biometric information, and wherein the user's biometric information comprises at least one of a heart rate, a heart rate variability, a calorie consumption, an oxygen saturation, a blood pressure, a fatigue, a stress, a blood sugar, a body water, an electrocardiogram, an electrodermal activity, a bioelectrical resistance analysis, an elapsed workout time for a user.

17. The method of claim 12, further comprising:

photographing a user's workout scene using a camera module for taking a user's workout image in real time or according to specified time intervals; and acquiring the user's workout image.

18. The method of claim 12, further comprising:

activating a health management app for acquiring the at least one workout-related information; and at least partially controlling the first external electronic device based on the health management app.

19. The method of claim 12, further comprising:

performing inter-process communication (IPC) interworking between the workout management app and a health management app;

acquiring messenger information of another user; and transmitting a message between the workout management app and the health management app based on the acquired messenger information.

20. The method of claim 12, further comprising:

activating a mirroring app for displaying the training program screen;

making an automatic connection with a second external electronic device to display a screen corresponding to the training program screen; and at least partially controlling the second external electronica-display device to display the screen based on the mirroring app, wherein the second external electronic device comprises a display device including a display configured to display the screen.

* * * * *